United States Patent [19]

Wentland et al.

[11] Patent Number: 4,499,091

[45] Date of Patent: Feb. 12, 1985

[54] 1-AMINO (OR SUBSTITUTED AMINO)-1,4-DIHYDRO-4-OXO-6-FLUORO-7-HETERYLQUINOLINE-3-CARBOXYLIC ACIDS AND THEIR USE AS ANTIBACTERIAL AGENTS

[75] Inventors: Mark P. Wentland, North Greenbush; Denis M. Bailey, East Greenbush, both of N.Y.

[73] Assignee: Sterling Drug Inc., New York, N.Y.

[21] Appl. No.: 466,095

[22] Filed: Feb. 14, 1983

Related U.S. Application Data

[63] Continuation-in-part of Ser. No. 363,876, Mar. 31, 1982, abandoned.

[51] Int. Cl.$^3$ .............. A61K 31/47; C07D 401/04; C07D 413/04; C07D 417/04
[52] U.S. Cl. .................... 514/254; 514/222; 514/233; 514/236; 514/212; 514/312; 544/58.6; 544/128; 544/363; 546/156; 260/244.4
[58] Field of Search ............ 544/363, 58.6, 128; 546/156; 424/250, 258, 246, 248.54, 248.55; 260/244.4

[56] References Cited

U.S. PATENT DOCUMENTS

| | | | |
|---|---|---|---|
| 4,146,719 | 3/1979 | Irikura | 544/363 |
| 4,284,629 | 8/1981 | Grohe et al. | 424/251 |
| 4,292,317 | 9/1981 | Pesson | 544/363 |

*Primary Examiner*—Glennon H. Hollrah
*Assistant Examiner*—James H. Turnipseed
*Attorney, Agent, or Firm*—Thomas L. Johnson; B. Woodrow Wyatt; Paul E. Dupont

[57] ABSTRACT

Novel 1-R-1,4-dihydro-4-oxo-6-fluoro-7-(Z=N—)-quinolinecarboxylic acids and esters thereof, where R is amino, lower-alkylamino, 2-propenylamino or di-lower-alkylamino, R'' is hydrogen or lower-alkyl, and Z=N is a heterocyclic group, useful as antibacterial agents, are prepared by reacting the corresponding 7-chloroquinoline derivatives with the appropriate heterocyclic compound, Z=NH. A preferred group of compounds are those where Z=N is 1-piperazinyl or 4-lower-alkyl-1-piperazinyl.

33 Claims, No Drawings

1-AMINO (OR SUBSTITUTED AMINO)-1,4-DIHYDRO-4-OXO-6-FLUORO-7-HETERYLQUINOLINE-3-CARBOXYLIC ACIDS AND THEIR USE AS ANTIBACTERIAL AGENTS

This application is a continuation-in-part of application Ser. No. 363,876, filed Mar. 31, 1982, now abandoned.

BACKGROUND OF THE INVENTION (1) Field of the Invention

The present invention relates to novel quinolone compounds, their use as antibacterial agents, and methods for the preparation thereof.

(2) Description of the Prior Art

Certain substituted-4-quinolone-3-carboxylic acids are known to possess antibacterial activity. Illustrative of these compounds are those of the formula:

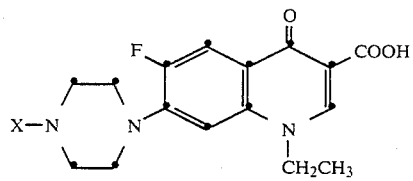

where X is hydrogen (Kyorin Seiyaku U.S. Pat. No. 4,146,719, Mar. 27, 1979) or methyl (R. Bellon/Dainippon U.S. Pat. No. 4,292,317, Sept. 29, 1981).

Bayer AG U.S. Pat. No. 4,284,629 (Aug. 18, 1981) discloses certain 4-quinolone-3-carboxylic acids having a tertiary-amino substituent in the 1-position, stated to possess antibacterial activity. Exemplary of the compounds disclosed are 1-dimethylamino-6-nitro-2-methyl-4-quinolone-3-carboxylic acid, methyl ester (Example 4); 1-dimethylamino-7-chloro-6-nitro-2-methyl-4-quinolone-3-carboxylic acid, methyl ester (Example 5); and 1-dimethylamino-7-(n-butylmercapto)-6-nitro-2-methyl-4-quinolone-3-carboxylic acid, methyl ester (Example 17). There is no disclosure of compounds having a heterocyclic group in the 7-position.

SUMMARY OF THE INVENTION

In a product aspect, the invention relates to compounds of the formula

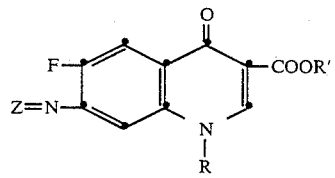

wherein R is amino, lower-alkylamino, 2-propenylamino, N-formyl-lower-alkylamino or di-lower-alkylamino; R' is hydrogen or lower-alkyl; and Z=N— is a heterocyclic group selected from the group consisting of:

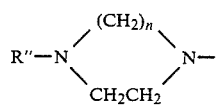

where n is 2–3, and R″ is hydrogen, lower-alkyl or acetyl;

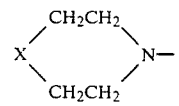

where X is O or S;

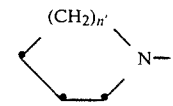

where n' is 1–3; and

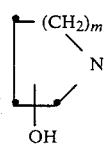

where m is 1–2;

a pharmaceutically acceptable acid-addition salt thereof; or an alkali metal or amine salt of a compound where R' is hydrogen.

A preferred class of compounds are those where Z=N— in Formula I is 1-piperazinyl or 4-lower-alkyl-1-piperazinyl of the formula:

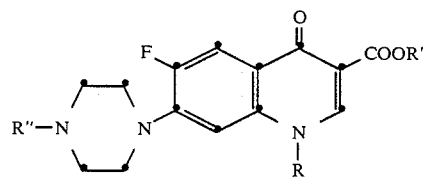

where R″ is hydrogen or lower-alkyl. Particularly preferred species are the compound where R is methylamino, R' is hydrogen and R″ is methyl; and its pharmaceutically acceptable salts.

In a further product aspect, the invention relates to compounds of the formula:

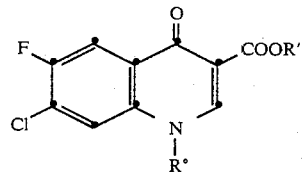

wherein R' is hydrogen or lower-alkyl, and R° is amino, lower-alkylamino, 2-propenylamino, di-lower-alkylamino, N-formylamino, N-formyl-lower-alkylamino or N-formyl-2-propenylamino. The compounds of Formula II are intermediates for the compounds of Formula I.

In a still further product aspect, the invention relates to compositions for combatting bacteria which comprise an antibacterially effective amount of a compound of Formula I together with one or more pharmaceutically acceptable excipients.

In a process aspect, the invention relates to a process for preparing a compound of Formula I which comprises reacting a compound of Formula II where R° is amino, lower-alkylamino, 2-propenylamino or di-lower-alkylamino with a compound of the formula Z=NH.

In a further process aspect, the invention relates to a method for combatting bacteria, which comprises contacting the locus of said bacteria with a composition comprising an antibacterially effective amount of a compound of Formula I.

DETAILED DESCRIPTION INCLUSIVE OF PREFERRED EMBODIMENTS

In the definition of the variables in Formulas I and II above, the term "lower-alkyl" stands for alkyl preferably having from one to three carbon atoms, thus including methyl, ethyl, propyl and isopropyl.

The amino function is introduced into the 1-position of the quinolone nucleus by treatment of the known starting material of the formula

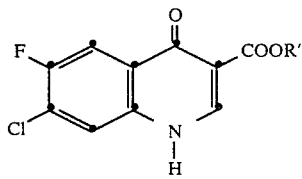

where R' is lower-alkyl, with an aminating agent, e.g. chloramine or an O-arylhydroxylamine such as O-(2,4-dinitrophenyl)hydroxylamine [2,4-$(O_2N)_2C_6H_3ONH_2$]; cf. Tamura et al., J. Org. Chem. 38, 1239 (1973). This results in a compound of Formula II where R° is $NH_2$ (Formula III below). The reaction takes place at ambient temperature in an inert organic solvent in the presence of a base such as potassium carbonate.

The synthesis of compounds of Formula I proceeds as follows:

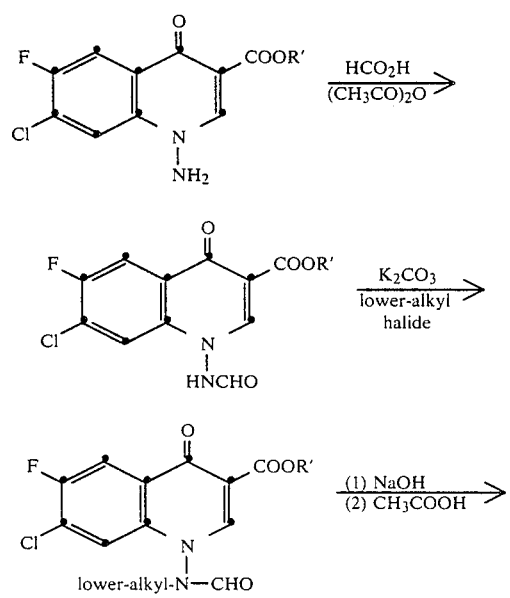

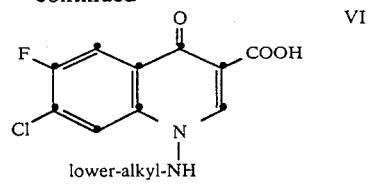

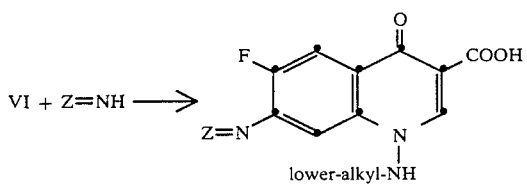

I (R is lower-alkylamino, R' is H)

In the foregoing flow-sheet, structure III is formylated with a mixture of formic acid and acetic anhydride to give the N-formyl derivative IV. IV is then alkylated with a lower-alkyl halide, preferably the iodide or bromide, in the presence of a base such as potassium carbonate to afford an N-lower-alkyl-N-formyl compound V. Hydrolysis of the latter with a base such as sodium hydroxide and acidification of the reaction mixture yields the N-lower-alkyl carboxylic acid VI.

The final step is the reaction of a compound of Formula VI with the appropriate heterocyclic compound, Z=NH, to give a compound of Formula I where R is lower-alkylamino and R' is hydrogen. The reaction takes place by heating the reactants together at a temperature between about 100° and about 150° C. in the presence of an acid acceptor to take up the hydrogen chloride formed in the reaction. The acid acceptor can be an alkali metal carbonate or a tertiary amine such as pyridine, triethylamine or (diisopropyl)ethylamine. Alternatively, an excess of heterocyclic reactant can be used as the acid acceptor. A preferred procedure is to heat at reflux temperature a mixture of the reactants in pyridine, or another solvent such as 2-methoxyethanol, using from 3 to 6 moles of heterocyclic reactant per mole of compound VI.

The compounds of Formula I where R is 2-propenylamino are prepared by an entirely analogous procedure using allyl halide in place of the lower-alkyl halide in the conversion of IV to V.

Referring back to the above flow-sheet, if desired, the compound of Formula III where R' is lower-alkyl can be hydrolyzed to the free acid (R' is hydrogen). The latter can be formylated to the N-formyl compound (IV, R' is hydrogen). The subsequent alkylation of IV (R'=H) will, however, also esterify the carboxyl group to form V (R' is lower-alkyl). Lower-alkyl esters of VI can be prepared by conventional esterification reactions or by selective hydrolysis of V (R' is lower-alkyl). The lower-alkyl esters of VI are potential intermediates for the preparation of compounds of Formula I where R' is lower-alkyl; but since there is a tendency to form amides upon the reaction of esters of VI with Z=NH, it is preferred to prepare the esters of Formula I by direct esterification of the free acids of Formula I.

The compounds of Formula I where R is amino ($NH_2$) are prepared by reacting the intermediate of Formula III with Z=NH.

The compounds of Formula I where R is N-formyl-lower-alkylamino are prepared by formylation of compounds of Formula I where R is lower-alkylamino.

The compounds of Formula I where R is di-lower-alkylamino are prepared as follows. A lower-alkyl ester of a compound of Formula VI is N-alkylated by heating it with a di-lower-alkyl sulfate to form a compound of Formula II where R' is lower-alkyl and R° is di-lower-alkylamino. Hydrolysis with aqueous alkali produces a compound of Formula II where R' is hydrogen and R° is di-lower-alkylamino. The latter is then reacted with a heterocyclic compound, Z=NH, to yield the desired compound of Formula I where R is di-lower-alkylamino. It will be apparent that this synthetic route allows the preparation of compounds where the lower-alkyl groups of di-lower-alkylamino are different, e.g., methylethylamino.

The invention also contemplates pharmaceutically acceptable acid-addition salts of the compounds of Formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like. Although the compounds of Formula I theoretically possess more than one basic nitrogen atom, the compounds tend to form only stable mono-acid-addition salts.

The compounds of Formula I where R' is hydrogen can also be prepared and used in the form of their alkali metal or amine salts, preferably the sodium, potassium or N-methylglucamine salts.

The following examples will further illustrate the invention.

PREPARATION 1

(a) Ethyl 1-amino-7-chloro-6-fluoro-1,4-dihydro-4-oxo-3-quinolinecarboxylate [III; R'=$C_2H_5$]

A mixture of 15.0 g (0.0556 mole) of ethyl 7-chloro-6-fluoro-1,4-dihydro-4-oxo-3-quinolinecarboxylate, 15.3 g (0.1112 mole) of potassium carbonate and 500 ml of dimethylformamide was stirred at room temperature for six hours. O-(2,4-Dinitrophenyl)hydroxylamine (14.3 g, 0.072 mole) was then added and the reaction mixture was stirred for about sixteen hours. Thin layer chromatography (tlc) indicated the reaction to be incomplete, so an additional 5.0 g of O-(2,4-dinitrophenyl)hydroxylamine was added and stirring continued for two hours. At that point an additional 2.8 g of O-(2,4-dinitrophenyl)hydroxylamine was added and stirring continued for two hours. The solvent was removed in vacuo at 50° C., and the residue stirred two hours with 600 ml of water and filtered. The resulting solid was slurried in 700 ml of refluxing acetonitrile and filtered. The filtrate upon cooling caused crystallization of 5.4 g of ethyl 1-amino-7-chloro-6-fluoro-1,4-dihydro-4-oxo-3-quinolinecarboxylate, m.p. 254°–258° C. The solid left on the filter was recrystallized from dimethylformamide to give an additional 6.7 g of pure product, total yield 12.1 g.

(b) 1-Amino-7-chloro-6-fluoro-1,4-dihydro-4-oxo-3-quinolinecarboxylic acid [III; R'=H]

Sodium hydroxide (0.91 g, 0.0228 mole) was dissolved in 100 ml of water, and 2.6 g (0.0091 mole) of ethyl 1-amino-7-chloro-6-fluoro-1,4-dihydro-4-oxo-3-quinolinecarboxylate was added. The mixture was stirred on a steam bath for two hours and the hot solution was neutralized with acetic acid (1.6 ml). The suspension of solid was stirred at room temperature for about sixteen hours, and the solid was collected by filtration and washed with water. The product was recrystallized from dimethylformamide to give 2.0 g of 1-amino-7-chloro-6-fluoro-1,4-dihydro-4-oxo-3-quinolinecarboxylic acid, beige powder, m.p. 312°–315° C.

1-Amino-7-chloro-6-fluoro-1,4-dihydro-4-oxo-3-quinolinecarboxylic acid can alternatively be prepared by amination of 7-chloro-6-fluoro-1,4-dihydro-4-oxo-3-quinolinecarboxylic acid by the procedure of Preparation 1(a). The latter acid was prepared by hydrolysis of ethyl 7-chloro-6-fluoro-1,4-dihydro-4-oxo-3-quinolinecarboxylate with aqueous sodium hydroxide and obtained in the form of a colorless solid, m.p. 274° C. (decompn.).

PREPARATION 2

Ethyl 7-chloro-6-fluoro-1-(formylamino)-1,4-dihydro-4-oxo-3-quinolinecarboxylate [IV; R'=$C_2H_5$]

Formic acid (24.5 ml, 0.625 mole) was added dropwise to 59 ml (0.625 mole) of acetic anhydride with stirring at 0° C. After the addition was complete the mixture comprising formic-acetic anhydride was stirred 15 min at 0° C. and 15 min at 50° C., and then cooled to 0° C. again. To this was added dropwise a solution of 17.8 g (0.0625 mole) of ethyl 1-amino-7-chloro-6-fluoro-1,4-dihydro-4-oxo-3-quinolinecarboxylate (Preparation 1a) in 130 ml of formic acid. The reaction mixture was stirred at room temperature for three and one-half days. At this time, tlc showed the presence of a small amount of starting material; therefore, an additional 48 ml of mixed anhydride was added to the reaction mixture which was then stirred for six hours longer. The solid product was collected by filtration and washed well with water to give 19.65 g of solid. The latter was recrystallized from a dimethylformamide-ethanol mixture and dried at 110° C. over phosphorus pentoxide for two and one-half days to give ethyl 7-chloro-6-fluoro-1-(formylamino)-1,4-dihydro-4-oxo-3-quinolinecarboxylate, m.p. 263°–264° (decompn.).

Similarly, 1-amino-7-chloro-6-fluoro-1,4-dihydro-4-oxo-3-quinolinecarboxylic acid can be formylated to give 7-chloro-6-fluoro-1-(formylamino)-1,4-dihydro-4-oxo-3-quinolinecarboxylic acid [IV; R'=H].

PREPARATION 3A

Ethyl 7-chloro-6-fluoro-1,4-dihydro-5-[(formyl)methylamino]-4-oxo-3-quinolinecarboxylate [V; lower-alkyl=$CH_3$, R'=$C_2H_5$]

A mixture of 14.65 g (0.047 mole) of ethyl 7-chloro-6-fluoro-1-(formylamino)-1,4-dihydro-4-oxo-3-quinolinecarboxylate (Preparation 2), 12.9 g (0.094 mole) of potassium carbonate and 200 ml of dimethylformamide was stirred at 25° C. for 90 minutes. Methyl iodide (20.0 g, 0.141 mole) was then added and the reaction mixture was stirred at room temperature for 90 minutes. The dimethylformamide was removed in high vacuum at 50° C., and the residue was partitioned between 250 ml of water and 500 ml of chloroform. The chloroform layer was separated and dried over anhydrous magnesium sulfate. There was obtained from the chloroform solution upon concentration 13.8 g of ethyl 7-chloro-6-fluoro-1,4-dihydro-5-[(formyl)methylamino]-4-oxo-3-quinolinecarboxylate, m.p. 213°–216° C.

PREPARATION 3B

Ethyl 7-chloro-6-fluoro-5-[(formyl)ethylamino]-1,4-dihydro-4-oxo-3-quinolinecarboxylate [V; lower-alkyl=$C_2H_5$, R'=$C_2H_5$] was prepared from 12 g of ethyl 7-chloro-6-fluoro-1-(formylamino)-1,4-dihydro-4-oxo-3-quinolinecarboxylate, 10.5 g of potassium carbonate and 9.4 ml of ethyl iodide in 163 ml of dimethylformamide according to the procedure of Preparation 3A above. There was obtained 11.5 g of product, tan powder, m.p. 185°–187° C.

PREPARATION 3C

Ethyl 7-chloro-6-fluoro-5-[(formyl)propylamino]-1,4-dihydro-4-oxo-3-quinolinecarboxylate [V; lower-alkyl=$(CH_2)_2CH_3$, R'=$C_2H_5$] was prepared from 12 g of ethyl 7-chloro-6-fluoro-1-(formylamino)-1,4-dihydro-4-oxo-3-quinolinecarboxylate, 10.5 g of potassium carbonate and 10.6 ml of n-propyl bromide in 163 ml of dimethylformamide according to the procedure of Preparation 3A above. There was obtained 12 g of product, pale yellow powder, m.p. 185°–187° C.

PREPARATION 3D

Ethyl 7-chloro-6-fluoro-5-[formyl(1-methylethyl)amino]-1,4-dihydro-4-oxo-3-quinolinecarboxylate [V; lower-alkyl=$(CH_3)_2CH$, R'=$C_2H_5$] was prepared from 11.3 g of ethyl 7-chloro-6-fluoro-1-(formylamino)-1,4-dihydro-4-oxo-3-quinolinecarboxylate, 8 g of potassium carbonate and 8.3 ml of isopropyl bromide in 122 ml of dimethylformamide according to the procedure of Preparation 3A above. There was obtained 10 g of product, tan powder, m.p. 148°–155° C.

PREPARATION 3E

Ethyl 7-chloro-6-fluoro-1-[formyl(2-propenyl)amino]-1,4-dihydro-4-oxo-3-quinolinecarboxylate [II; R'=$C_2H_5$, R°=OCH—N($CH_2CH=CH_2$)] was prepared from 10 g of ethyl 7-chloro-6-fluoro-1-(formylamino)-1,4-dihydro-4-oxo-3-quinolinecarboxylate, 8.8 g of potassium carbonate and 8.4 ml of allyl bromide in 137 ml of dimethylformamide according to the procedure of Preparation 3A above. There was obtained 9.4 g of product, light orange powder, m.p. 178°–182° C.

PREPARATION 4A

7-Chloro-6-fluoro-1,4-dihydro-1-methylamino-4-oxo-3-quinolinecarboxylic acid [VI; lower-alkyl=$CH_3$]

A mixture of 11.8 g of ethyl 7-chloro-6-fluoro-1,4-dihydro-5-[(formyl)methylamino]-4-oxo-3-quinolinecarboxylate (Preparation 3A), 5.8 g of sodium hydroxide and 300 ml of water was stirred on a steam bath for two hours. The reaction mixture was decolorized with activated charcoal, and the warm solution after filtration was acidified with 9.5 g of acetic acid. The mixture was stirred at 0° C. for 30 minutes and the solid product was collected by filtration and washed with water. The product was recrystallized from 150 ml of dimethylformamide to give 8.7 g of 7-chloro-6-fluoro-1,4-dihydro-1-methylamino-4-oxo-3-quinolinecarboxylic acid, light yellow crystals, m.p. 275°–279° C. (decompn.).

7-Chloro-6-fluoro-1,4-dihydro-1-methylamino-4-oxo-3-quinolinecarboxylic acid was found to have antibacterial activity when tested according to the biological procedures described hereinafter. It was active in vitro against *Escherichia coli, Klebsiella pneumoniae* and *Proteus mirabilis* at minimal inhibitory concentrations (MIC) of 1.0, 1.95 and 1.0 mcg/ml, respectively. It was active in vivo in the mouse against *E. coli* and *K. pneum.* at fifty percent protective dose levels of 56 and 186 mg/kg, respectively.

PREPARATION 4B

7-Chloro-1-ethylamino-6-fluoro-1,4-dihydro-4-oxo-3-quinolinecarboxylic acid [VI; lower-alkyl=$C_2H_5$]

A solution of 10 g (0.029 mole) of ethyl 7-chloro-6-fluoro-5-[(formyl)ethylamino]-1,4-dihydro-4-oxo-3-quinolinecarboxylate (Preparation 3B) in 260 ml of absolute ethanol was heated to reflux and a solution of 4.3 g (0.068 mole) of 85% potassium hydroxide in 14.5 ml of water was added. About 100 ml of 95% ethanol was then added, and the reaction mixture was stirred and refluxed for one hour. The mixture was filtered while hot and the collected solid washed with absolute ethanol and with ether, and dried in vacuo at 70° C. to give 5.4 g of 7-chloro-1-ethylamino-6-fluoro-1,4-dihydro-4-oxo-3-quinolinecarboxylic acid in the form of its potassium salt hemihydrate, m.p. 258° C. (decompn.). An additional 3.8 g, m.p. 260°–262° C. was obtained from the alcohol filtrates.

7-Chloro-1-ethylamino-6-fluoro-1,4-dihydro-4-oxo-3-quinolinecarboxylic acid was found to have antibacterial activity in vitro against *S. aureus* (MIC=15.6 mcg/ml), *E. coli* (MIC=1.95 mcg/ml), *K. pneum.* (MIC=3.9 mcg/ml), *P. mirabilis* (MIC=3.9 mcg/ml), *P. vulgaris* (MIC=0.25 mcg/ml), *P. aeruginosa* (MIC=31.3 mcg/ml), and *S. pyogenes* (MIC=31.3 mcg/ml).

PREPARATION 4C

7-Chloro-6-fluoro-1,4-dihydro-4-oxo-1-propylamino-3-quinolinecarboxylic acid [VI; lower-alkyl=$(CH_2)_2CH_3$] was prepared from 10.5 g of ethyl 7-chloro-6-fluoro-5-[(formyl)propylamino]-1,4-dihydro-4-oxo-3-quinolinecarboxylate (Preparation 3C) and 4.4 g of 85% potassium hydroxide in ethanol solution according to the procedure described above in Preparation 4B. There was obtained 5.7 g of product in the form of its potassium salt hemihydrate, m.p. 267° C. (decompn.).

7-Chloro-6-fluoro-1,4-dihydro-4-oxo-1-propylamino-3-quinolinecarboxylic acid was found to have antibacterial activity in vitro against *S. aureus* (MIC=15.6 mcg/ml), *E. coli* (MIC=15.6 mcg/ml), *K. pneum.* (MIC=31.3 mcg/ml), *P. vulgaris* (MIC=3.9 mcg/ml), and *S. pyogenes* (MIC=15.6 mcg/ml).

PREPARATION 4D

7-Chloro-6-fluoro-1,4-dihydro-4-oxo-1-(2-propenylamino)-3-quinolinecarboxylic acid [II; R'=H, R°=HN$CH_2CH=CH_2$] was prepared from 8.4 g of ethyl 7-chloro-6-fluoro-1-[formyl(2-propenyl)amino]-1,4-dihydro-4-oxo-3-quinolinecarboxylate (Preparation 3E) and 5.5 g of sodium hydroxide according to the procedure described above in Preparation 4A. There was obtained 6.96 g of product in the form of a hydrate (4:1), m.p. 240°–242° C.

PREPARATION 5

Ethyl 7-chloro-6-fluoro-1,4-dihydro-1-methylamino-4-oxo-3-quinolinecarboxylate [II; R°=CH₃NH, R'=C₂H₅]

A mixture of 148 g of ethyl 7-chloro-6-fluoro-1,4-dihydro-1-[(formyl)methylamino]-4-oxo-3-quinolinecarboxylate, 70 g of sodium hydroxide and 3 liters of water was stirred at 60° C. for three and one-half hours. At this point the reaction mixture contained a considerable amount of insoluble material which was collected by filtration, giving 23 g of solid. The latter was slurried in 2.5 liters of boiling ethanol and filtered through a steam funnel. Upon cooling the filtrate there separated 12.4 g of ethyl 7-chloro-6-fluoro-1,4-dihydro-1-methylamino-4-oxo-3-quinolinecarboxylate, m.p. 202°–207° C. A further recrystallization from ethanol gave a sample as a tan powder, m.p. 206°–209° C.

The corresponding methyl ester (II; R°=CH₃NH, R'=CH₃), m.p. 228°–232° C., was obtained by transesterification of the ethyl ester with methanol.

PREPARATION 6

7-Chloro-1-dimethylamino-6-fluoro-1,4-dihydro-4-oxo-3-quinolinecarboxylic acid [II; R°=(CH₃)₂N, R'=H]

A mixture of 5 g of ethyl 7-chloro-6-fluoro-1,4-dihydro-1-methylamino-4-oxo-3-quinolinecarboxylate (Preparation 5) and 50 ml of dimethyl sulfate was stirred at 100° C. for about sixteen hours. The reaction mixture was allowed to stand for two days at room temperature and then poured into 500 ml of ice-water containing about 75 g of potassium carbonate. The mixture was stirred for one hour, and the solid product was collected by filtration, slurried in tetrahydrofuran, again collected and dried to give 1.3 g of product, m.p. 243°–248° C., comprising mixed ethyl and methyl ester of 7-chloro-1-dimethylamino-6-fluoro-1,4-dihydro-4-oxo-3-quinolinecarboxylic acid. A 0.5 g portion of the mixed ester was added to 13 ml of water containing 0.128 g of sodium hydroxide, and the mixture was stirred on a steam bath for two hours. The reaction mixture was filtered hot and acidified with acetic acid. The solid product which separated was collected, washed with water and dried in vacuo to give 0.22 g of 7-chloro-1-dimethylamino-6-fluoro-1,4-dihydro-4-oxo-3-quinolinecarboxylic acid, m.p. 255°–256° C.

EXAMPLE 1

6-Fluoro-1,4-dihydro-1-methylamino-7-(4-methyl-1-piperazinyl)-4-oxo-3-quinolinecarboxylic acid [IA; R=CH₃NH, R'=H, R''=CH₃]

A mixture of 5.0 g (0.0185 mole) of 7-chloro-6-fluoro-1,4-dihydro-1-methylamino-4-oxo-3-quinolinecarboxylic acid (Preparation 4A), 7.4 g (0.0739 mole) of N-methylpiperazine and 30 ml of pyridine was refluxed under nitrogen for 15 hours. The reaction mixture was then cooled and the solid material collected by filtration and washed with ether. The 4.3 g of product thus obtained was recrystallized from 125 ml of boiling dimethylformamide, collected, washed with dimethylformamide and ether and dried at 70° C. in high vacuum for a day to give 4.0 g of 6-fluoro-1,4-dihydro-1-methylamino-7-(4-methyl-1-piperazinyl)-4-oxo-3-quinolinecarboxylic acid, colorless powder, m.p. 299°–301° C. (decompn.).

6-Fluoro-1,4-dihydro-1-methylamino-7-(4-methyl-1-piperazinyl)-4-oxo-3-quinolinecarboxylic acid was converted to its monohydrochloride salt, m.p. above 300° C., by boiling it with an equimolar quantity of aqueous hydrochloric acid.

6-Fluoro-1,4-dihydro-1-methylamino-7-(4-methyl-1-piperazinyl)-4-oxo-3-quinolinecarboxylic acid was converted to its methanesulfonate salt, m.p. 287°–289° C. (decompn.), by treating it with a slight excess of aqueous methanesulfonic acid, and when solution was complete adding acetone to precipitate out the salt. The salt was recrystallized from aqueous acetonitrile.

6-Fluoro-1,4-dihydro-1-methylamino-7-(4-methyl-1-piperazinyl)-4-oxo-3-quinolinecarboxylic acid was converted to its fumarate salt, m.p. 253°–254° C. (decompn.), by heating it with an equimolar quantity of fumaric acid in aqueous medium. The salt separated upon cooling.

6-Fluoro-1,4-dihydro-1-methylamino-7-(4-methyl-1-piperazinyl)-4-oxo-3-quinolinecarboxylic acid was converted to its sodium salt monohydrate, m.p. 256° C. (decompn.) by treating it with an equimolar quantity of aqueous sodium hydroxide containing some ethanol to aid in dissolution. The product obtained by evaporation of the solvent was crystallized from aqueous acetone.

6-Fluoro-1,4-dihydro-1-methylamino-7-(4-methyl-1-piperazinyl)-4-oxo-3-quinolinecarboxylic acid was converted to its 4'-oxide, m.p. 231° C. (decompn.) by treating an aqueous solution of its sodium salt with two molar equivalents of hydrogen peroxide, stirred 20 hours at 45° C. The solution was treated with 50 mg of palladium on carbon catalyst to remove excess hydrogen peroxide and then acidified to obtain the oxidized product. The 4'-oxide was found to have antibacterial activity in vitro against *E. coli* (MIC=16 mcg/ml), *K. pneum.* (MIC=32 mcg/ml) and *P. mirab.* (MIC=32 mcg/ml).

EXAMPLE 1A

The preparation of the compound of Example 1 was carried out on a larger scale as follows: A mixture of 52 g (0.192 mole) of 7-chloro-6-fluoro-1,4-dihydro-1-methylamino-4-oxo-3-quinolinecarboxylic acid, 53 ml (0.478 mole) of N-methylpiperazine and 260 ml of pyridine was heated at reflux for about sixteen hours. Additional N-methylpiperazine (10 ml) was then added and the refluxing continued for six hours. The reaction mixture was cooled, and the solid product collected by filtration and washed with cold pyridine and ether to yield 46 g of material. The latter was combined with another run starting with 5 g of 7-chloro compound and recrystallized from dimethylformamide, washed with cold dimethylformamide and ether and dried in vacuo at 80° C. to give 48.5 g of 6-fluoro-1,4-dihydro-1-methylamino-7-(4-methyl-1-piperazinyl)-4-oxo-3-quinolinecarboxylic acid, m.p. above 300° C.

EXAMPLE 1B

The compound of Example 1 was prepared on a still larger scale as follows: A mixture of 970 g of 7-chloro-6-fluoro-1,4-dihydro-1-methylamino-4-oxo-3-quinolinecarboxylic acid, 1600 ml of N-methylpiperazine and 8 liters of 2-methoxyethanol was heated to reflux (about 127° C.) over a period of three hours. After 20 hours at reflux, the reaction mixture was cooled to 10° C. and filtered. The filter cake was washed with cold methoxyethanol, followed by methanol. The product was dried at 40° C., affording 925 g of 6-fluoro-1,4-dihydro-1-methylamino-7-(4-methyl-1-piperazinyl)-4-oxo-3-quinolinecarboxylic acid which was purified in the form of its methanesulfonate salt.

EXAMPLE 2

1-Amino-6-fluoro-1,4-dihydro-4-oxo-7-(1-piperazinyl)-3-quinolinecarboxylic acid [IA; $R=NH_2$, $R'=H$, $R''=H$] was prepared from 2.8 g of 1-amino-7-chloro-6-fluoro-1,4-dihydro-4-oxo-3-quinolinecarboxylic acid (Preparation 1b) and 4.7 g of piperazine in 150 ml of pyridine according to the procedure described above in Example 1A. The product was converted to its 4-methylbenzenesulfonate salt, m.p. 293°–295° C. (decompn.) when recrystallized from water.

EXAMPLE 3

1-Amino-6-fluoro-1,4-dihydro-4-oxo-7-(4-methyl-1-piperazinyl)-3-quinolinecarboxylic acid [IA; $R=NH_2$, $R'=H$, $R''=CH_3$] was prepared from 2.3 g of 1-amino-7-chloro-6-fluoro-1,4-dihydro-4-oxo-3-quinolinecarboxylic acid (Preparation 1b) and 3.6 g of N-methylpiperazine in 125 ml of pyridine according to the procedure described above in Example 1A. The product (1.9 g) was obtained as a pale orange powder, m.p. 303°–306° C. (decompn.) when recrystallized from dimethylformamide.

EXAMPLE 4

6-Fluoro-1,4-dihydro-1-methylamino-4-oxo-7-(1-piperazinyl)-3-quinolinecarboxylic acid [IA; $R=CH_3NH$, $R'=H$, $R''=H$] was prepared from 20.3 g of 7-chloro-6-fluoro-1,4-dihydro-1-methylamino-4-oxo-3-quinolinecarboxylic acid (Preparation 4A) and 64.5 g of piperazine in 850 ml of pyridine according to the procedure of Example 1. There was obtained 17.9 g of product as a pale yellow solid, m.p. 288°–290° C. (decompn.), when recrystallized from dimethylformamide.

A sample of the foregoing compound [IA; $R=CH_3NH$, $R'$ and $R''=H$] was treated with aqueous p-methylbenzenesulfonic acid to produce the 4-methylbenzenesulfonate salt, m.p. 278°–280° C. (decompn.), straw-colored crystals from water.

EXAMPLE 5

1-Ethylamino-6-fluoro-1,4-dihydro-7-(4-methyl-1-piperazinyl)-4-oxo-3-quinolinecarboxylic acid [IA; $R=C_2H_5NH$, $R'=H$, $R''=CH_3$] was prepared from 4.7 g of 7-chloro-1-ethylamino-6-fluoro-1,4-dihydro-4-oxo-3-quinolinecarboxylic acid (Preparation 4B) and 7.3 ml of N-methylpiperazine in 18.5 ml of pyridine according to the procedure of Example 1. There was obtained 3.7 g of product, m.p. 255°–256° C.

EXAMPLE 6

6-Fluoro-1,4-dihydro-7-(4-methyl-1-piperazinyl)-4-oxo-1-propylamino-3-quinolinecarboxylic acid [IA; $R=CH_3(CH_2)_2NH$, $R'=H$, $R''=CH_3$] was prepared from 5 g of 7-chloro-6-fluoro-1,4-dihydro-4-oxo-1-propylamino-3-quinolinecarboxylic acid (Preparation 4C) and 7.4 ml of N-methylpiperazine in 19 ml of pyridine according to the procedure of Example 1. There was obtained 3.7 g of product, m.p. 210°–212° C.

EXAMPLE 7

6-Fluoro-1-dimethylamino-1,4-dihydro-7-(4-methyl-1-piperazinyl)-4-oxo-3-quinolinecarboxylic acid [IA; $R=(CH_3)_2N$, $R'=H$, $R''=CH_3$] was prepared from 1.65 g of 7-chloro-1-dimethylamino-6-fluoro-1,4-dihydro-4-oxo-3-quinolinecarboxylic acid (Preparation 6) and 2.64 ml of N-methylpiperazine in 6.6 ml of pyridine according to the procedure of Example 1. There was obtained 0.9 g of product, m.p. 253°–255° C. as a light tan powder.

EXAMPLE 8

7-(4-Ethyl-1-piperazinyl)-6-fluoro-1,4-dihydro-1-methylamino-4-oxo-3-quinolinecarboxylic acid [IA; $R=CH_3NH$, $R'=H$, $R''=C_2H_5$] was prepared from 3.5 g of 7-chloro-6-fluoro-1,4-dihydro-1-methylamino-4-oxo-3-quinolinecarboxylic acid (Preparation 4A) and 5.9 g of N-ethylpiperazine in 14.4 ml of pyridine according to the procedure of Example 1. There was obtained 2.5 g of product as a pale yellow powder, m.p. 260° C.

EXAMPLE 9

Ethyl 6-fluoro-1,4-dihydro-1-methylamino-7-(4-methyl-1-piperazinyl)-4-oxo-3-quinolinecarboxylate [IA; $R=CH_3NH$, $R'=C_2H_5$, $R''=CH_3$]

A slurry of 3.5 g (0.0105 mole) of 6-fluoro-1,4-dihydro-1-methylamino-7-(4-methyl-1-piperazinyl)-4-oxo-3-quinolinecarboxylic acid in 500 ml of absolute ethanol was heated to reflux while stirring. Methanesulfonic acid (3.1 g, 0.0313 mole) was added and the resulting clear yellow solution was heated at reflux for three days. The ethanol was evaporated off, the residue taken up in 50 ml of water, and the solution neutralized by gradual addition of sodium bicarbonate (6 g). The product which separated was collected by filtration and washed with 200 ml of water. To a slurry of the product in 30 ml of water was added 1.2 g of methanesulfonic acid. The resulting clear yellow solution was filtered and diluted with 200 ml of acetone which caused crystallization of 3.0 g of ethyl 6-fluoro-1,4-dihydro-1-methylamino-7-(4-methyl-1-piperazinyl)-4-oxo-3-quinolinecarboxylate in the form of its methanesulfonate salt, m.p. 255° C. (decompn.) after being dried at 65° C. in vacuo for a day.

EXAMPLE 10

6-Fluoro-1,4-dihydro-1-methylamino-7-[4-(1-methylethyl)-1-piperazinyl]-4-oxo-3-quinolinecarboxylic acid [IA; $R=CH_3NH$, $R'=H$, $R''=(CH_3)_2CH$] was prepared from 5 g of 7-chloro-6-fluoro-1,4-dihydro-1-methylamino-4-oxo-3-quinolinecarboxylic acid (Preparation 4A) and 14.6 g of N-isopropylpiperazine dihydrochloride according to the procedure of Example 1 except that (diisopropyl)ethylamine (70 ml) was used in place of pyridine. There was obtained 2.4 g of product as a grayish tan solid, m.p. 245°–250° C.

EXAMPLE 11

6-Fluoro-1,4-dihydro-1-methylamino-4-oxo-7-(4-propyl-1-piperazinyl)-3-quinolinecarboxylic acid [IA; $R=CH_3NH$, $R'=H$, $R''=CH_3CH_2CH_2$] was prepared from 5 g of 7-chloro-6-fluoro-1,4-dihydro-1-methylamino-4-oxo-3-quinolinecarboxylic acid (Preparation 4A) and 21.5 g of N-propylpiperazine dihydrobromide according to the procedure of Example 1 except that (diisopropyl)ethylamine (45 ml) was used in place of pyridine. There was obtained 4.8 g of product, m.p. 272°–277° C.

EXAMPLE 12

6-Fluoro-1,4-dihydro-7-(4-methyl-1-piperazinyl)-4-oxo-1-(2-propenylamino)-3-quinolinecarboxylic acid [IA; R=CH$_2$=CHCH$_2$NH, R'=H, R"=CH$_3$] was prepared from 5.9 g of 7-chloro-6-fluoro-1,4-dihydro-4-oxo-1-(2-propenylamino)-3-quinolinecarboxylic acid (Preparation 4D) and 8.7 ml of N-methylpiperazine in 22.3 ml of pyridine according to the procedure of Example 1. There was obtained 2.8 g of product as a pale yellow powder, m.p. 220°–222° C.

EXAMPLE 13

6-Fluoro-1,4-dihydro-1-methylamino-7-(4-morpholinyl)-4-oxo-3-quinolinecarboxylic acid [I; R=CH$_3$NH, R'=H, Z=N=4-morpholinyl] was prepared from 5 g of 7-chloro-6-fluoro-1,4-dihydro-1-methylamino-4-oxo-3-quinolinecarboxylic acid (Preparation 4A) and 10 ml of morpholine in 40 ml of pyridine according to the procedure of Example 1. There was obtained 3.7 g of product as a colorless to pale yellow powder, m.p. 288°–289° C.

EXAMPLE 14

7-(4-Acetyl-1-piperazinyl)-6-fluoro-1,4-dihydro-1-methylamino-4-oxo-3-quinolinecarboxylic acid [I; R=CH$_3$NH, R'=H, Z=N=4-acetyl-1-piperazinyl] was prepared from 4.3 g of 7-chloro-6-fluoro-1,4-dihydro-1-methylamino-4-oxo-3-quinolinecarboxylic acid (Preparation 4A) and 6.5 g of N-acetylpiperazine in 35 ml of pyridine according to the procedure of Example 1. There was obtained 3 g of product, m.p. 295°–300° C.

EXAMPLE 15

6-Fluoro-1,4-dihydro-1-methylamino-4-oxo-7-(1-piperidinyl)-3-quinolinecarboxylic acid [I; R=CH$_3$NH, R'=H, Z=N=1-piperidinyl] was prepared from 4.8 g of 7-chloro-6-fluoro-1,4-dihydro-1-methylamino-4-oxo-3-quinolinecarboxylic acid (Preparation 4A) and 14.8 ml of piperidine in 50 ml of pyridine according to the procedure of Example 1. There was obtained 1.7 g of product, m.p. 208°–211° C. when recrystallized from dimethylformamide.

EXAMPLE 16

6-Fluoro-1,4-dihydro-1-methylamino-4-oxo-7-(1-pyrrolidinyl)-3-quinolinecarboxylic acid [I; R=CH$_3$NH, R'=H, Z=N=1-pyrrolidinyl] was prepared from 5 g of 7-chloro-6-fluoro-1,4-dihydro-1-methylamino-4-oxo-3-quinolinecarboxylic acid (Preparation 4A) and 12.5 ml of pyrrolidine in 50 ml of pyridine according to the procedure of Example 1. There was obtained 2.3 g of product as a yellow powder, m.p. 314°–318° C. when recrystallized from dimethylformamide.

EXAMPLE 17

6-Fluoro-1,4-dihydro-7-(4-hydroxy-1-piperidinyl)-1-methylamino-4-oxo-3-quinolinecarboxylic acid [I; R=CH$_3$NH, R'=H, Z=N=4-hydroxy-1-piperidinyl] was prepared from 5 g of 7-chloro-6-fluoro-1,4-dihydro-1-methylamino-4-oxo-3-quinolinecarboxylic acid (Preparation 4A) and 7.2 g of 4-hydroxypiperidine in 30 ml of pyridine according to the procedure of Example 1. There was obtained 2.6 g of product, colorless to pale yellow powder, m.p. 230°–236° C. when recrystallized from dimethylformamide.

EXAMPLE 18

6-Fluoro-1,4-dihydro-7-(3-hydroxy-1-piperidinyl)-1-methylamino-4-oxo-3-quinolinecarboxylic acid [I; R=CH$_3$NH, R'=H, Z=N=3-hydroxy-1-piperidinyl] was prepared from 5 g of 7-chloro-6-fluoro-1,4-dihydro-1-methylamino-4-oxo-3-quinolinecarboxylic acid (Preparation 4A) and 7.2 g of 3-hydroxypiperidine in 30 ml of pyridine according to the procedure of Example 1. There was obtained 1.8 g of product, m.p. 180° C. when recrystallized first from acetic acid and then from acetonitrile.

EXAMPLE 19

6-Fluoro-7-(hexahydro-1H-1,4-diazapin-1-yl)-1,4-dihydro-1-methylamino-4-oxo-3-quinolinecarboxylic acid [I; R=CH$_3$NH, R"=H, Z=N=hexahydro-1H-1,4-diazapin-1-yl] was prepared from 6 g of 7-chloro-6-fluoro-1,4-dihydro-1-methylamino-4-oxo-3-quinolinecarboxylic acid (Preparation 4A) and 22 g of hexahydro-1,4-diazapine in 240 ml of pyridine according to the procedure of Example 1. There was obtained 1.3 g of product in the form of its hydrochloride salt, yellow powder, m.p. 305° C. (decompn.).

EXAMPLE 20

6-Fluoro-7-(hexahydro-4-methyl-1H-1,4-diazapin-1-yl)-1,4-dihydro-1-methylamino-4-oxo-3-quinolinecarboxylic acid [I; R=CH$_3$NH, R"=H, Z=N=hexahydro-4-methyl-1H-1,4-diazapin-1-yl] was prepared from 5 g of 7-chloro-6-fluoro-1,4-dihydro-1-methylamino-4-oxo-3-quinolinecarboxylic acid (Preparation 4A) and 8.3 g of hexahydro-4-methyl-1,4-diazapine in 30 ml of pyridine according to the procedure of Example 1. There was obtained 1.7 g of product in the form of its hydrochloride hemihydrate, pale yellow powder, m.p. 288° C.

EXAMPLE 21

6-Fluoro-1,4-dihydro-1-methylamino-4-oxo-7-(4-thiomorpholinyl)-3-quinolinecarboxylic acid [I; R=CH$_3$NH, R"=H, Z=N=4-thiomorpholinyl] was prepared from 3.5 g of 7-chloro-6-fluoro-1,4-dihydro-1-methylamino-4-oxo-3-quinolinecarboxylic acid (Preparation 4A) and 6.5 ml of thiomorpholine in 80 ml of pyridine according to the procedure of Example 1. There was obtained 2 g of product, pale yellow solid, m.p. 260°–261° C. when recrystallized from dimethylformamide.

EXAMPLE 22

6-Fluoro-1,4-dihydro-7-(3-hydroxy-1-pyrrolidinyl)-1-methylamino-4-oxo-3-quinolinecarboxylic acid [I; R=CH$_3$NH, R"=H, Z=N=3-hydroxy-1-pyrrolidinyl] was prepared from 7.7 g of 7-chloro-6-fluoro-1,4-dihydro-1-methylamino-4-oxo-3-quinolinecarboxylic acid (Preparation 4A) and 9.75 g of 3-hydroxypyrrolidine in 30 ml of pyridine according to the procedure of Example 1. There was obtained 4.7 g of product as a yellow powder, m.p. 319°–321° C. (decompn.) when recrystallized from dimethylformamide.

EXAMPLE 23

6-Fluoro-1-(N-formylmethylamino)-1,4-dihydro-7-(4-methyl-1-piperazinyl)-4-oxo-3-quinolinecarboxylic acid [IA; R=CH$_3$NCHO, R'=H, R"=CH$_3$]

6-Fluoro-methylamino-1,4-dihydro-7-(4-methyl-1-piperazinyl)-4-oxo-3-quinolinecarboxylic acid (Example 1) (2.7 g) was added to mixed formic-acetic anhydride prepared from 3.9 g of 96% formic acid and 8.3 g of acetic anhydride. The reaction mixture was stirred at room temperature for 16 hours and then concentrated in vacuo. The solid residue was dissolved in 50 ml of water and the solution made basic with pyridine. The solid product was collected by filtration and recrystallized from acetonitrile to give 2.0 g of 6-fluoro-1-(N-formylmethylamino)-1,4-dihydro-7-(4-methyl-1-piperazinyl)-4-oxo-3-quinolinecarboxylic acid, cream-colored powder, m.p. 252°–253° C. (decompn.).

The in vitro antibacterial activity of the compounds of the invention was determined by conventional serial dilution procedures. Bacterial cultures were grown in tryptose phosphate broth or brain heart infusion broth (containing heat-inactivated normal horse serum for tests with *S. pyogenes*) overnight at 37° C. and subsequently diluted in double strength broth to provide bacterial inocula of about 2×10$^5$ cells/ml. Aqueous solutions of the compounds of the invention were prepared by dissolving the free acid form in 0.5N sodium hydroxide. The solutions were diluted with sterile distilled water to 1000 mcg/ml of compound in terms of the free acid. Serial two-fold dilutions of the compound stock solutions were prepared in water and 0.5 ml of each dilution was transferred to sets of tubes, one set for each bacterial inoculum. Each tube was then inoculated with 0.5 ml of the appropriate culture, resulting in a final bacterial concentration of about 1×10$^5$ cells/ml.

The minimal inhibitory concentration (MIC), defined as the lowest concentration of the test compound to inhibit visible bacterial growth, was recorded after 18–20 hours of static incubation at 37° C. The results are recorded in Table I:

TABLE I

| Bacteria | Minimal Inhibitory Concentration (mcg/ml) Compound Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| *Staphylococcus aureus* Smith | 3.9 | 31.3 | 7.8 | 2.0 | 3.9 | 15.6 | 3.9 | 1.0 | 500 | 2 | 1.95 |
| *Streptococcus pyogenes* C203 | 7.8 | 250 | 62.5 | 7.8 | 31.3 | 125 | 31.3 | 3.9 | >500 | 4 | 7.8 |
| *Escherichia coli* Vogel | 0.25 | 3.9 | 2.0 | 1.0 | 0.5 | 2.0 | 0.5 | 0.5 | 62.5 | 0.5 | 0.25 |
| *Klebsiella pneumoniae* 39645 | 0.25 | 7.8 | 2.0 | 1.0 | 0.5 | 2.0 | 2.0 | 0.5 | 62.5 | 0.5 | 0.5 |
| *Proteus mirabilis* MGH-1 | 0.5 | 7.8 | 2.0 | 0.5 | 3.9 | 31.3 | 2.0 | 1.0 | 12.5 | 4 | 1.0 |
| *Proteus vulgaris* 9920 | 0.125 | 3.9 | 1.0 | 0.25 | 0.25 | 2.0 | 0.12 | 0.25 | 31.3 | | 0.25 |
| *Pseudomonas aeruginosa* MGH-2 | 1.0 | 62.5 | 15.6 | 1.0 | 7.8 | 31.3 | 2.0 | 2.0 | 500 | 8 | 7.8 |

| Bacteria | Minimal Inhibitory Concentration (mcg/ml) Compound Example No. | | | | | | | | | | | |
|---|---|---|---|---|---|---|---|---|---|---|---|---|
| | 12 | 13 | 14 | 15 | 16 | 17 | 18 | 19 | 20 | 21 | 22 | 23 |
| *Staphylococcus aureus* Smith | 7.8 | 1.0 | 3.9 | 1.95 | 0.5 | 1.95 | 1.95 | 7.8 | 4 | 0.5 | 1 | 15.6 |
| *Streptococcus pyogenes* C203 | 62.5 | 15.6 | 31.3 | >7.8 | >7.8 | 31.3 | 15.6 | 31.3 | 32 | >8 | 16 | 250 |
| *Escherichia coli* Vogel | 1.0 | 0.5 | 15.6 | 3.9 | 1.0 | 1.95 | 3.9 | 3.9 | 2 | 0.5 | 1 | 1.95 |
| *Klebsiella pneumoniae* 39645 | 1.95 | 1.95 | 7.8 | 7.8 | 3.9 | 7.8 | 7.8 | 15.6 | 4 | 0.5 | 4 | 1.95 |
| *Proteus mirabilis* MGH-1 | 7.8 | 3.9 | 15.6 | 7.8 | 3.9 | 3.9 | 7.8 | 1.95 | 2 | 2 | 1 | 3.9 |
| *Proteus vulgaris* 9920 | 1.0 | 0.125 | 1.95 | 0.5 | 0.5 | 0.125 | 0.25 | 1.0 | | | | 1.0 |
| *Pseudomonas aeruginosa* MGH-2 | 15.6 | 15.6 | 62.5 | >7.8 | >7.8 | 7.8 | 31.3 | 7.8 | 4 | 4 | 4 | 7.8 |

The in vivo antibacterial activity of the compounds of the invention was determined in female mice, 18–20 grams each, by the following procedure:

Aqueous solutions of the compounds to be tested were prepared by dissolving the free acid form in dilute sodium hydroxide and diluting the solution with distilled water to be desired volume.

Cultures of *Escherichia coli* Vogel prepared in brain heart infusion broth, cultures of *Klebsiella pneumoniae* 39645 grown in tryptose phosphate broth with 5% rabbit serum diluted in the same broth and cultures of *Pseudomonas aeruginosa* MGH-2 grown on brain heart infusion agar and suspended in physiological saline, were used to infect the mice as follows:

*E. coli* and *P. aeruginosa*: mice were inoculated intraperitoneally with 0.5 ml of the bacterial test inoculum (1.87×10$^7$ and 5×10$^6$ cells/ml respectively).

*K. pneumoniae*: mice were inoculated intramuscularly in the right hind leg with 0.2 ml of the bacterial test inoculum (2.05×10$^4$ cells/ml).

Mice infected with *E. coli* were medicated once (0.5 ml) one-half hour post infection, the test compound being administered by either the subcutaneous (s.c.) or oral (p.o.) route. Deaths were recorded daily for seven days.

Mice infected with *K. pneumoniae* were medicated at the following times: seventeen hours and one hour preinfection, six hours postinfection and twice a day for the next three days. The test compound was administered by both subcutaneous (0.2 ml) and oral (0.5 ml) routes. Deaths were recorded daily for fourteen days.

Mice infected with *P. aeruginosa* were medicated at one-half, four and seven hours postinfection. The test compounds were administered by either subcutaneous (0.2 ml) or oral (0.5 ml) routes. Deaths were recorded daily for seven days.

Groups of ten animals each for four or five dose levels were thus treated and the number of survivors in each group recorded. The fifty percent protective dose values (PD$_{50}$) were then calculated. The results obtained are given in Table II:

TABLE II

| Compound Example No. | Protective Dose (PD$_{50}$, mg/kg) | | | | | |
|---|---|---|---|---|---|---|
| | E. coli | | K. pneumoniae | | P. aeruginosa | |
| | s.c. | p.o. | s.c. | p.o. | s.c. | p.o. |
| 1 | 0.55 | 1.03 | 8.8 | 10.6 | 2.50 | 3.13 |
| 2 | >200 | | >200 | | | |
| 3 | 3.13 | | 30.5 | | | |
| 4 | 0.32 | | 6.25 | | 0.46 | |
| 5 | 4.1 | | 90 | | | |
| 6 | 32 | | >200 | | | |
| 7 | 1.66 | | 29 | | | |
| 8 | 1.4 | | 15.1 | | | |
| 9 | 4.4 | | >200 | | | |
| 10 | 2.7 | | 50 | | | |
| 11 | 14.8 | | 81.5 | | | |
| 12 | 18.9 | | 141 | | | |
| 13 | 16.3 | | 200 | | | |
| 14 | 100 | | 100 | | | |
| 15 | >200 | | >200 | | | |
| 16 | >200 | | >200 | | | |
| 17 | 12.5 | | 200 | | | |
| 18 | 38 | | >200 | | | |
| 19 | 2.5 | | >50 | | | |
| 20 | 3.6 | | 33 | | | |
| 21 | >200 | | | | | |
| 22 | 10.4 | | 118 | | | |
| 23 | 10.4 | | >200 | | | |

The compounds of the invention which are active in vitro but are relatively ineffective in vivo can be used for topical application and for disinfection of inanimate objects.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. A compound of the formula

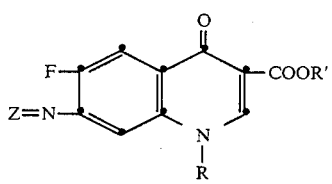

wherein R is amino, lower-alkylylamino, 2-propenylamino, N-formyl-lower-alkylamino or di-lower-alkylamino; R' is hydrogen or lower-alkyl; and Z=N— is a heterocyclic group selected from the group consisting of:

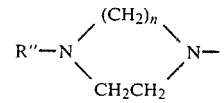

where n is 2-3, and R" is hydrogen, lower-alkyl or acetyl;

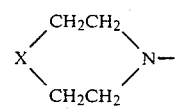

where X is O or S;

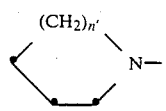

where n' is 1-3; and

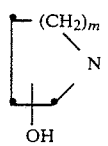

where m is 1-2;

a pharmaceutically acceptable acid-addition salt thereof; or an alkali metal or amine salt of a compound where R' is hydrogen.

2. A compound according to claim 1 of the formula

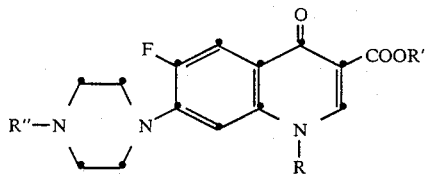

wherein R is amino, lower-alkylamino, 2-propenylamino, N-formyl-lower-alkylamino or di-lower-alkylamino; and R' and R" are hydrogen or lower-alkyl; a pharmaceutically acceptable acid-addition salt thereof; or an alkali metal or amine salt of a compound where R' is hydrogen.

3. A compound according to claim 2 wherein R is lower-alkylamino and R' is hydrogen.

4. 6-Fluoro-1,4-dihydro-1-methylamino-7-(4-methyl-1-piperazinyl)-4-oxo-3-quinolinecarboxylic acid or a pharmaceutically acceptable salt thereof, according to claim 3.

5. 1-Amino-6-fluoro-1,4-dihydro-4-oxo-7-(1-piperazinyl)-3-quinolinecarboxylic acid, according to claim 2.

6. 1-Amino-6-fluoro-1,4-dihydro-4-oxo-7-(4-methyl-1-piperazinyl)-3-quinolinecarboxylic acid, according to claim 2.

7. 6-Fluoro-1,4-dihydro-1-methylamino-4-oxo-7-(1-piperazinyl)-3-quinolinecarboxylic acid, according to claim 3.

8. 1-Ethylamino-6-fluoro-1,4-dihydro-7-(4-methyl-1-piperazinyl)-4-oxo-3-quinolinecarboxylic acid, according to claim 3.

9. 6-Fluoro-1,4-dihydro-7-(4-methyl-1-piperazinyl)-4-oxo-1-propylamino-3-quinolinecarboxylic acid, according to claim 3.

10. 6-Fluoro-1-dimethylamino-1,4-dihydro-7-(4-methyl-1-piperazinyl)-4-oxo-3-quinolinecarboxylic acid, according to claim 2.

11. 7-(4-Ethyl-1-piperazinyl)-6-fluoro-1,4-dihydro-1-methylamino-4-oxo-3-quinolinecarboxylic acid, according to claim 3.

12. 6-Fluoro-1,4-dihydro-1-methylamino-7-[4-(1-methylethyl)-1-piperazinyl]-4-oxo-3-quinolinecarboxylic acid, according to claim 3.

13. 6-Fluoro-1,4-dihydro-1-methylamino-4-oxo-7-(4-propyl-1-piperazinyl)-3-quinolinecarboxylic acid, according to claim 3.

14. 6-Fluoro-1,4-dihydro-7-(4-methyl-1-piperazinyl)-4-oxo-1-(2-propenylamino)-3-quinolinecarboxylic acid, according to claim 2.

15. 6-Fluoro-1,4-dihydro-1-methylamino-7-(4-morpholinyl)-4-oxo-3-quinolinecarboxylic acid, according to claim 1.

16. 7-(4-Acetyl-1-piperazinyl)-6-fluoro-1,4-dihydro-1-methylamino-4-oxo-3-quinolinecarboxylic acid, according to claim 1.

17. 6-Fluoro-1,4-dihydro-1-methylamino-4-oxo-7-(1-piperidinyl)-3-quinolinecarboxylic acid, according to claim 1.

18. 6-Fluoro-1,4-dihydro-1-methylamino-4-oxo-7-(1-pyrrolidinyl)-3-quinolinecarboxylic acid, according to claim 1.

19. 6-Fluoro-1,4-dihydro-7-(4-hydroxy-1-piperidinyl)-1-methylamino-4-oxo-3-quinolinecarboxylic acid, according to claim 1.

20. 6-Fluoro-1,4-dihydro-7-(3-hydroxy-1-piperidinyl)-1-methylamino-4-oxo-3-quinolinecarboxylic acid, according to claim 1.

21. 6-Fluoro-7-(hexahydro-1H-1,4-diazapin-1-yl)-1,4-dihydro-1-methylamino-4-oxo-3-quinolinecarboxylic acid, according to claim 1.

22. 6-Fluoro-7-(hexahydro-4-methyl-1H-1,4-diazapin-1-yl)-1,4-dihydro-1-methylamino-4-oxo-3-quinolinecarboxylic acid, according to claim 1.

23. 6-Fluoro-1,4-dihydro-1-methylamino-4-oxo-7-(4-thiomorpholinyl)-3-quinolinecarboxylic acid, according to claim 1.

24. 6-Fluoro-1,4-dihydro-7-(3-hydroxy-1-pyrrolidinyl)-1-methylamino-4-oxo-3-quinolinecarboxylic acid, according to claim 1.

25. 6-Fluoro-1-(N-formylmethylamino)-1,4-dihydro-7-(4-methyl-1-piperazinyl)-4-oxo-3-quinolinecarboxylic acid, according to claim 2.

26. A compound having the formula

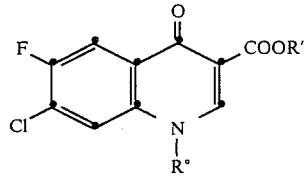

wherein R' is hydrogen or lower-alkyl, and R° is amino, lower-alkylamino, 2-propenylamino, di-lower-alkylamino, N-formylamino, N-formyl-lower-alkylamino or N-formyl-2-propenylamino.

27. A compound according to claim 26 wherein R° is amino.

28. A compound according to claim 26 wherein R° is lower-alkylamino and R' is hydrogen.

29. 7-Chloro-6-fluoro-1,4-dihydro-1-methylamino-4-oxo-3-quinolinecarboxylic acid, according to claim 28.

30. A composition for combatting bacteria, which comprises an antibacterially effective amount of a compound according to claim 1 together with one or more pharmaceutically acceptable excipients.

31. A composition according to claim 30 wherein the antibacterially active compound is 6-fluoro-1,4-dihydro-1-methylamino-7-(4-methyl-1-piperazinyl)-4-oxo-3-quinolinecarboxylic acid or a pharmaceutically acceptable salt thereof.

32. A method for combatting bacteria, which comprises contacting the locus of said bacteria with a composition according to claim 30.

33. A method according to claim 32 wherein the antibacterially active compound is 6-fluoro-1,4-dihydro-1-methylamino-7-(4-methyl-1-piperazinyl)-4-oxo-3-quinolinecarboxylic acid or a pharmaceutically acceptable salt thereof.

* * * * *

UNITED STATES PATENT AND TRADEMARK OFFICE
CERTIFICATE OF CORRECTION

PATENT NO. : 4,499,091
DATED : February 12, 1985
INVENTOR(S) : Mark P. Wentland and Denis M. Bailey It is certified that error appears in the above-identified patent and that said Letters Patent is hereby corrected as shown below:

Column 6, line 56, "-5-[(formyl)me-" should read -- -1-[(formyl)me- --.

Column 7, line 4, "-5-[(formyl)me-" should read -- -1-[(formyl)me- --.

Column 7, line 9, "-5-[(formyl)ethylamino]" should read -- -1-[(formyl)ethylamino]--.

Column 7, line 20, "-5-[(formyl)propylamino]" should read -- -1-[(formyl)propylamino]--.

Column 7, line 32, "-5-[formyl(1-methylethyl-" should read -- -1-[formyl(1-methylethyl- --.

Column 7, line 58, "-5-[(formyl)methylamino]" should read -- -1-[(formyl)methylamino]--.

Column 8, line 19, "-5-[(formyl)ethylamino]" should read -- -1-[(formyl)ethylamino]--.

Column 8, line 47, "-5-[(formyl)propylamino]" should read -- -1-[(formyl)propylamino]--.

Signed and Sealed this

Fifth Day of November 1985

[SEAL]

Attest:

DONALD J. QUIGG

Attesting Officer  Commissioner of Patents and Trademarks